United States Patent [19]
DeCoster et al.

[11] Patent Number: 5,908,589
[45] Date of Patent: Jun. 1, 1999

[54] METHODS FOR SEPARATING CATALYST FROM OXIDATION MIXTURES CONTAINING DIBASIC ACIDS

[75] Inventors: David C. DeCoster, Buckley, Wash.; Eustathios Vassiliou, Newark, Del.; Mark W. Dassel, Indianola, Wash.; Ader M. Rostami; Douglas J. Dudgeon, both of Bainbridge Island, Wash.

[73] Assignee: Twenty-First Century Research Corporation, Newark, Del.

[21] Appl. No.: 08/986,505

[22] Filed: Dec. 8, 1997

[51] Int. Cl.⁶ .............. D01D 1/02; D01D 5/08; D01F 13/00
[52] U.S. Cl. .................. 264/37.18; 264/176.1; 528/176; 528/288; 528/308; 528/322; 528/335
[58] Field of Search .............. 264/37.18, 176.1; 528/176, 288, 308, 322, 335

[56] References Cited

U.S. PATENT DOCUMENTS

| | | | |
|---|---|---|---|
| 1,121,532 | 12/1914 | Newberry . | |
| 2,014,044 | 9/1935 | Haswell | 75/17 |
| 2,223,493 | 12/1940 | Loder | 260/537 |
| 2,223,494 | 12/1940 | Loder | 260/586 |
| 2,301,240 | 11/1942 | Baumann et al. | 183/115 |
| 2,439,513 | 4/1948 | Hamblet et al. | 260/533 |
| 2,557,282 | 6/1951 | Hamblet et al. | 260/533 |
| 2,565,087 | 8/1951 | Porter et al. | 260/631 |
| 2,980,523 | 4/1961 | Dille et al. | 48/215 |
| 3,161,603 | 12/1964 | Leyshon et al. | 252/413 |
| 3,231,608 | 1/1966 | Kollar | 260/533 |
| 3,234,271 | 2/1966 | Barker et al. | 260/531 |
| 3,290,369 | 12/1966 | Bonfield et al. | 260/537 |
| 3,361,806 | 1/1968 | Lidov | 260/531 |
| 3,515,751 | 6/1970 | Oberster et al. | 260/533 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,839,435 | 10/1974 | Shigeyasu et al. | 260/524 R |
| 3,928,005 | 12/1975 | Laslo | 55/73 |
| 3,932,513 | 1/1976 | Russell | 260/586 AB |
| 3,946,076 | 3/1976 | Paasen et al. | 260/586 P |
| 3,957,876 | 5/1976 | Rapoport et al. | 260/586 P |
| 3,987,100 | 10/1976 | Barnette et al. | 260/586 P |
| 3,987,808 | 10/1976 | Carbonell et al. | 137/3 |
| 4,025,498 | 5/1977 | Buss et al. | 260/95 A |
| 4,039,304 | 8/1977 | Bechthold et al. | 55/10 |
| 4,055,600 | 10/1977 | Langley et al. | 260/586 |
| 4,065,527 | 12/1977 | Graber | 261/79 A |
| 4,308,037 | 12/1981 | Meissner et al. | 55/10 |
| 4,332,590 | 6/1982 | Smith | 23/230 A |
| 4,361,965 | 12/1982 | Goumondy et al. | 34/57 R |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |

(List continued on next page.)

FOREIGN PATENT DOCUMENTS

| | | |
|---|---|---|
| 439 007 A2 | 7/1991 | European Pat. Off. . |
| 729 084 A1 | 8/1996 | European Pat. Off. . |
| 729 085 A1 | 8/1996 | European Pat. Off. . |
| 751 105 A2 | 1/1997 | European Pat. Off. . |
| 2 722 783 A1 | 1/1996 | France . |
| 4426132A1 | 1/1996 | Germany . |
| 4427474 A1 | 2/1996 | Germany . |
| 48-003815 | 2/1973 | Japan . |
| 415172 | 8/1934 | United Kingdom . |
| 738808 | 10/1955 | United Kingdom . |
| 864106 | 3/1961 | United Kingdom . |
| 1143213 | 2/1969 | United Kingdom . |
| 2014473 | 8/1979 | United Kingdom . |
| WO96/03365 | 2/1996 | WIPO . |
| WO 96/40610 | 12/1996 | WIPO . |

OTHER PUBLICATIONS

U.S. Application No. 08/587,967, Filed Jan. 17, 1996.
U.S. Application No. 08/812,847, Filed Mar. 6, 1997.
U.S. Application No. 08/859,985, Filed May 21, 1997.
U.S. Application No. 08/861,281, Filed May 21, 1997.
U.S. Application No. 08/861,180, Filed May 21, 1997.
U.S. Application No. 08/861,176, Filed May 21, 1997.
U.S. Application No. 08/859,890, Filed May 21, 1997.
U.S. Application No. 08/861,210, Filed May 21, 1997.
U.S. Application No. 08/824,992, Filed Mar. 27, 1997.
U.S. Application No. 08/477,195, Filed Jun. 7, 1995.
U.S. Application No. 08/876,692, Filed Jun. 16, 1997.
U.S. Application No. 08/900,323, Filed Jul. 25, 1997.
U.S. Application No. 08/931,035, Filed Sep. 16, 1997.
U.S. Application No. 08/932,875, Filed Sep. 18, 1997.
U.S. Application No. 08/934,253, Filed Sep. 19, 1997.
E. Sorribes et al., "Formación de neuvas fases en el proceso de obtención de ácido adípico: causas y efectos que provocan," *Rev. R. Acad. Cienc. Exactas, Fis. Nat. Madrid* (1987), 81 (1), 233–5 (+ English language translation).

*Primary Examiner*—Leo B. Tentoni
*Attorney, Agent, or Firm*—Seed and Berry LLP

[57] ABSTRACT

This invention relates to methods and reactor devices for controlling the oxidation of hydrocarbons to dibasic acids, in the presence of a catalyst and a monobasic acid, by removing the catalyst from the reaction mixture, outside the oxidation zone, after the oxidation has taken place at least partially. Initially, the catalyst is partially precipitated and removed by reducing the water level in the reaction mixture and/or subjecting the reaction mixture to a temperature, at which or over which catalyst precipitates. After the initial partial precipitation of the catalyst, the mother liquor remaining is subjected to a thermal treatment during which at least the major part of the monobasic acid is removed leaving behind molten dibasic acids, in which the remaining catalyst precipitates substantially in its totality, and it is removed. The precipitated catalyst in the two precipitation stages may be recycled in miscellaneous ways. From the foregoing it will be appreciated that, although specific embodiments of the invention have been described herein for purposes of illustration, various modifications may be made without deviating from the spirit and scope of the invention. Accordingly, the invention is not limited except as by the appended claims.

61 Claims, 1 Drawing Sheet

U.S. PATENT DOCUMENTS

| | | | |
|---|---|---|---|
| 5,061,453 | 10/1991 | Krippl et al. | 422/106 |
| 5,104,492 | 4/1992 | King et al. | 203/15 |
| 5,123,936 | 6/1992 | Stone et al. | 55/8 |
| 5,170,727 | 12/1992 | Nielsen | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,516,423 | 5/1996 | Conoby et al. | 210/85 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |
| 5,756,837 | 5/1998 | Costantini et al. | 562/543 |

METHODS FOR SEPARATING CATALYST FROM OXIDATION MIXTURES CONTAINING DIBASIC ACIDS

TECHNICAL FIELD

This invention relates to methods of oxidizing hydrocarbons, such as cyclohexane for example, to respective dibasic acids, such as adipic acid for example, and more specifically, how to remove catalyst after the reaction, preferably for recycling.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process", the "Boric Acid Process", and the "Direct Synthesis Process", which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase." However, no attention has been paid so far to the importance of the two phases, except for separating the adipic acid from the "Polar Phase" and recycling these phases to the reactor partially or totally with or without further treatment.

It is also important to note that most studies on the Direct Synthesis Process have been conducted in a batch mode, literally or for all practical purposes.

As aforementioned, there is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among others, may be considered as representative of oxidation processes relative to the preparation of diacids and other intermediate oxidation products.

U.S. Pat. No. 5,463,119 (Kollar) discloses a process for the oxidative preparation of $C_5$–$C_8$ aliphatic dibasic acids by (1) reacting,
   (a) at least one saturated cycloaliphatic hydrocarbon having from 5 to 8 ring carbon atoms in the liquid phase and
   (b) an excess of oxygen gas or an oxygen-containing gas in the presence of
   (c) a solvent comprising an organic acid containing only primary and/or secondary hydrogen atoms and
   (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by (1) reacting, at a cycloaliphatic hydrocarbon conversion level of between about 7% and about 30%,
   (a) at least one saturated cycloaliphatic hydrocarbon having from 5 to 8 ring carbon atoms in the liquid phase and
   (b) an excess of oxygen gas or an oxygen containing gas mixture in the presence of
   (c) less than 1.5 moles of a solvent per mole of cycloaliphatic hydrocarbon (a), wherein said solvent comprises an organic acid containing only primary and/or secondary hydrogen atoms and
   (d) at least about 0.002 mole per 1000 grams of reaction mixture of a polyvalent heavy metal catalyst; and
(2) isolating the $C_5$–$C_8$ aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° C. to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid. from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3%–0.7%.

PCT International Publication WO 96/03365 (Constantini et al.) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5% to 15% relative to monobasic aliphatic acid solvent, and preferably 1% to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° C. and 160° C., while removing the water of reaction substantially as quickly as it is formed.

None of the above references, or any other references known to the inventors disclose, suggest or imply, singly or in combination, removal of catalyst, from hydrocarbon reaction mixtures, preferably for recycling, subject to the intricate and critical controls and requirements of the instant invention as described and claimed.

Our U.S. Pat. Nos. 5,580,531, 5,558,842, 5,502,245, 5,654,475, and our copending applications 08/477,195 (filed Jun. 7, 1995), 08/587,967 (filed Jun. 17, 1996), and published PCT patent application WO 96/07056, all of which are incorporated herein by reference, describe methods and apparatuses relative to controlling reactions in atomized liquids. Our copending applications Ser. No. 08/812,847, filed on Mar. 6, 1997; 08/824,992, filed on Mar. 27, 1997; 08/859,985, filed on May 21 1997; 08/861,281, filed on May 21 1997; 08/861,180, filed on May 21 1997; 08/861,176, filed on May 21 1997; 08/859,890, filed on May 21 1997; 08/861,210, filed on May 21 1997; 08/876,692, filed on Jun. 16 1997; 08/900,323, filed on Jul. 25 1997; 08/931,035, filed on Sep. 16, 1997; 08/932,875, filed on Sep. 18, 1997; and 08/934,253, filed on Sep. 19, 1997; are all also incorporated herein by reference.

All of our following PCT patent applications, are also incorporated herein by reference:

International Application No. PCT/US97/10830, filed on Jun. 23, 1997 of Mark W. Dassel, David C. DeCoster, Ader M. Rostami, Eustathios Vassiliou, and Sharon M. Aldrich, titled "Methods and Devices for Oxidizing a Hydrocarbon to Form an Acid"; and International Application No. PCT/US97/12944, filed on Jul. 23, 1997 of David C. DeCoster, Eustathios Vassiliou, Mark W. Dassel, Sharon M. Aldrich, and, Ader M. Rostami, titled "Methods and Devices for Controlling the Reaction Rate and/or Reactivity of Hydrocarbon to an Intermediate Oxidation Product by Adjusting the Oxidant Consumption Rate."

SUMMARY OF THE INVENTION

As aforementioned, this invention relates to methods of oxidizing hydrocarbons, such as cyclohexane for example, to respective intermediate oxidation products, such as adipic acid for example, and more specifically, how to remove catalyst after the reaction, preferably for recycling. More particularly, this invention pertains to a method of removing catalyst from a reaction mixture containing one or more dibasic acids, the reaction mixture having been formed after reaction of a hydrocarbon with an oxidant in the presence of the catalyst, water, and a monobasic acid solvent, in an oxidation zone, the method being characterized by steps of:

(a) precipitating part of the catalyst in a first catalyst precipitation zone by removing water at least partially from the reaction mixture and/or controlling temperature to be adequately high for causing partial catalyst precipitation;

(b) removing the precipitated catalyst, thus forming a second mother liquor comprising dissolved catalyst, monobasic acid solvent, and one or more of dibasic acids;

(c) removing at least partially the monobasic acid solvent and melting the one or more dibasic acids until catalyst precipitates in a second catalyst precipitation zone; and (d) removing the catalyst which precipitated in step (c).

The method may further comprise a step of recycling the catalyst precipitated in step (b) to the oxidation zone, and/or a step of recycling the catalyst removed in step (d) to the first catalyst precipitation zone, while part or all of one or more of dibasic acids may be removed before step (a).

The method may also comprise a step of forming a third mother liquor after removing the precipitated catalyst in step (d), and recycling part of the third mother liquor back to the second catalyst precipitation zone.

The present method is particularly applicable in the case that the hydrocarbon comprises a compound selected from a group consisting of cyclohexane, cyclohexanone, cyclohexanol, cyclohexylhydroperoxide, and a mixture thereof, the oxidant comprises oxygen, and one of the dibasic acids comprises adipic acid. The monobasic acid solvent is preferably acetic acid. Glutaric acid and succinic acid may also be part of the dibasic acids as by-products. In this case, it may be beneficial in adding glutaric acid to the second catalyst precipitation zone. The added glutaric acid may be obtained from the present process itself, or from any other source.

The method may further comprise a step of reacting at least one of the dibasic acids, adipic acid for example, with a reactant selected from a group consisting of a polyol, a polyamine, and a polyamide in a manner to form a polymer of a polyester, or a polyamide, or a (polyimide and/or polyamideimide), respectively. The polymer may be spun or otherwise take the form of fibers.

The instant invention further pertains a reactor device for conducting an oxidation of a hydrocarbon to a dibasic acid in the presence of a catalyst and a monobasic acid solvent, in a reaction mixture, followed by a two-stage separation of the catalyst from the reaction mixture, the reactor device characterized by:

an oxidation chamber;

a first catalyst precipitation assembly connected to the reaction chamber, the first catalyst precipitation assembly comprising at least one of a de-watering station, and a first thermal treatment station; and a second catalyst precipitation assembly connected to the first catalyst precipitation assembly, the second catalyst precipitation assembly comprising an evaporator and a second thermal treatment station.

The reactor device may further comprise a dibasic acid precipitation station disposed between the oxidation chamber and the first catalyst precipitation assembly. It may also comprise a dibasic acid separator disposed between the dibasic acid precipitation station and the first catalyst precipitation assembly, the dibasic acid separator being connected to the first catalyst precipitation station through a first mother liquor line, through which first mother liquor, separated from the precipitated dibasic, acid, may be transferred to the first catalyst precipitation assembly, the dibasic acid separator also being connected to a first solids removal line, through which the precipitated dibasic acid may be removed at least partially. It is preferable that the dibasic acid precipitation station comprises a flash-crystallizer.

A first catalyst separator is preferably disposed between the first catalyst precipitation assembly and the second catalyst precipitation assembly, the first catalyst separator being connected to the second catalyst precipitation station through a second mother liquor line, through which, second mother liquor, after having been separated from the precipitated catalyst, may be transferred to the second catalyst precipitation assembly. The first catalyst separator is preferably also connected to a second solids removal line, through which the precipitated catalyst may be removed at least partially.

It is also preferable that a second catalyst separator is disposed after the second catalyst precipitation assembly, the second catalyst separator being connected to a third mother liquor line. The second catalyst separator is preferably also connected to a third solids removal line, through which the precipitated catalyst may be removed at least partially.

Preferably, the second solids removal line is connected to the oxidation chamber directly or indirectly, so that precipitated catalyst from the first catalyst separator may be recycled to the oxidation chamber, and/or the third solids removal line is connected to the first catalyst precipitation assembly, so that precipitated catalyst may be recycled from the second catalyst separator to the first catalyst precipitation assembly. The precipitated catalyst may be pre-dissolved, preferably in acetic acid comprising small amounts of water, before it is recycled to the oxidation chamber. This operation may be preferably conducted in a heated stirred tank.

It is also preferable that the third mother liquor line is connected to a recycle mother liquor line, which in turn is connected to the second catalyst precipitation assembly, so that third mother liquor may be partially recycled from the second catalyst separator to the second catalyst precipitation assembly, if so desired.

All ratios and percentages are expressed by weight unless otherwise specified.

A controller, preferably a computerized controller, may handle with ease and accuracy the operation of the devices of the present invention. Programming a computerized controller to perform such functions is a routine process, well known to the art. According to this invention, a controller, based on information received, from a reaction or oxidation zone, for example, controls feed rates of raw materials and/or recycled materials, temperatures, pressures, and other parameters in order to achieve the desirable results. The controller may also be programmed, by techniques well known to the art, to include flow sheet simulation, which may account for vapor/liquid equilibrium and energy balance effects.

As aforementioned, these methods and devices are particularly suited in the case that the hydrocarbon comprises cyclohexane, the mixture comprises acetic acid, and the catalyst comprises a cobalt salt.

BRIEF DESCRIPTION OF THE DRAWINGS

The reader's understanding of this invention will be enhanced by reference to the following detailed description taken in combination with the drawing figure, wherein.

DETAILED DESCRIPTION OF THE INVENTION

Figure 1:
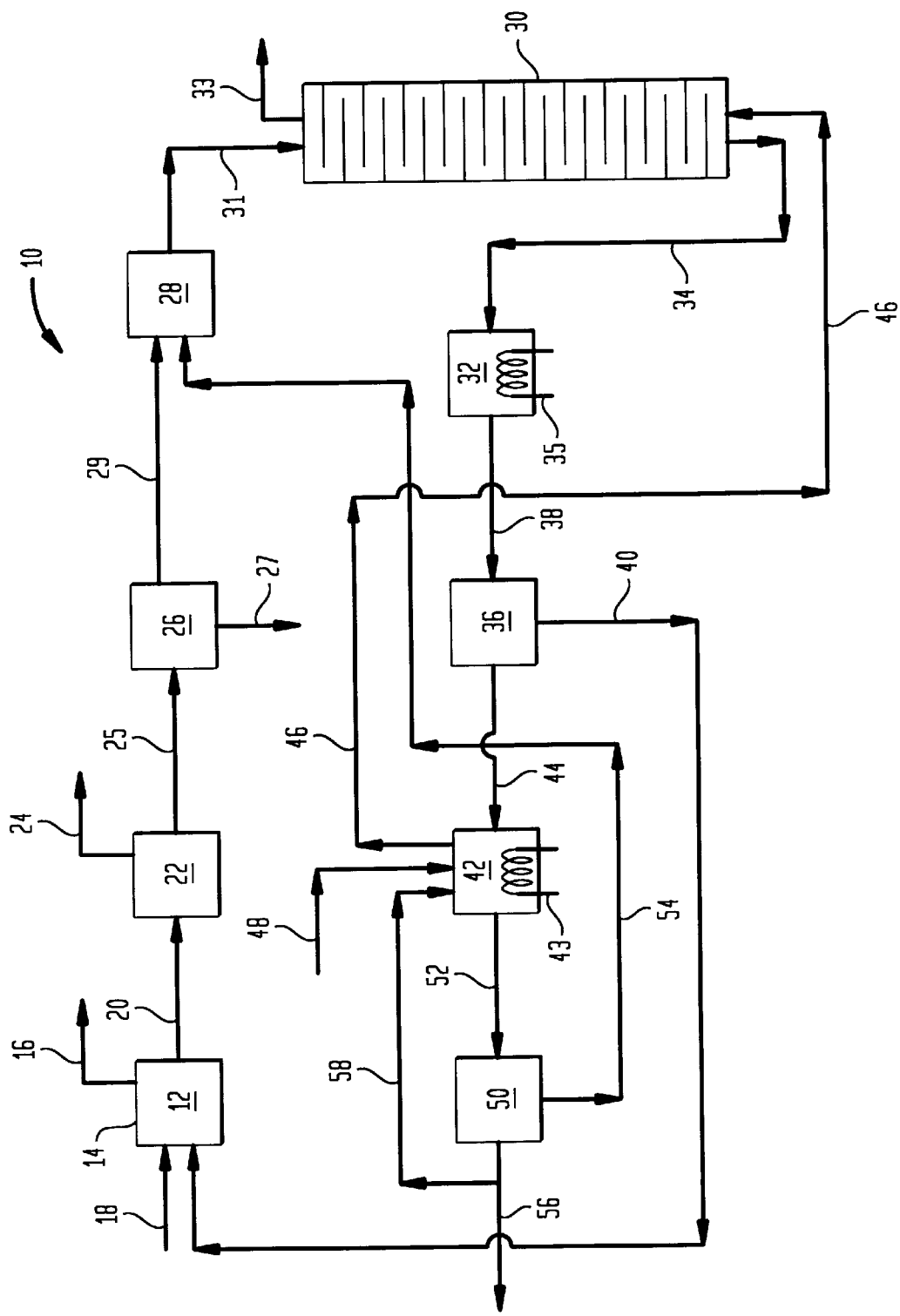
FIG. 1 illustrates a block diagram of a preferred embodiment of the present invention.

As aforementioned, this invention relates to methods and devices for oxidizing hydrocarbons, such as cyclohexane for example, to respective dibasic acids, such as adipic acid for example, and more specifically, how to remove catalyst after the reaction, preferably for recycling.

Proper catalyst handling in oxidation reactions has always been a considerable problem in the art. According to the present invention, catalyst is precipitated from the reaction mixture, after an oxidation has taken place by a two stage process, involving precipitation in a molten mixture containing dibasic acids, after partial catalyst precipitation caused by de-watering and/or thermal treatment. It is important that the molten mixture is adequately non-viscous for the catalyst separation. It was found by the inventors that addition of adjuncts in the molten mixture, such as glutaric acid for example, considerably help in achieving workable viscosities.

Preferably, the catalyst which is precipitated from the molten mixture is recycled to the stage of de-watering and/or thermal treatment, as is explained in more detail herein, although it is possible to be recycled to the oxidation chamber, if so desired for some reason. Recycling of the precipitated catalyst to the stage of de-watering and/or thermal treatment presents enormous advantages, because the precipitated catalyst may be easily and efficiently recycled for repeated utilization, without substantial recycling of dibasic acids to the oxidation chamber.

De-watering is preferably conducted by use of distillation columns and/or addition of anhydrides, preferably acetic acid anhydride. However, other methods, such as for example use of other de-watering compounds, are not excluded and may be used very effectively, especially in combination with distillation columns. Examples of other de-watering compounds are colloidal silica, calcium oxide, molecular sieves, etc.

It has been found by the inventors that very important factors regarding partial catalyst precipitation in a reaction mixture are water level, catalyst level, hydrocarbon level, and temperature, among others, which include reaction products and by-products. For a given set of factors, partial catalyst precipitation is facilitated as the water level decreases, the catalyst level increases, the hydrocarbon level increases, and as temperature increases.

For better clarification of this invention, the examples given below assume that the hydrocarbon is cyclohexane, the intermediate oxidation product comprises adipic acid, the mixture contains a solvent comprising acetic acid, and the catalyst comprises a cobalt compound. It should be understood, however, that the teachings of this invention are applicable to different hydrocarbons, intermediate oxidation products, solvents, and catalysts than the ones used in the examples. Only minor modifications may be needed to fit each individual case.

Referring now to FIG. 1, there is depicted a reactor device or system 10, comprising an oxidation chamber 12 containing an oxidation zone 14. The reactor device 10 is only partially shown for demonstrating the components necessary to exemplify the present invention. Miscellaneous treatment, product or by-product separation, recycling, etc. devices, well known to the art, are not shown for purposes of clarity and brevity. Also devices connected to the oxidation reactor 12, such as for example distillation columns, condensers, re-boilers, etc., are not shown, also for purposes of brevity and clarity, and they are represented in this particular example by oxidation chamber exit line 16. The oxidation reactor 12 may be any type of reactor, such as for example stirred tank reactor, atomization reactor, recirculation reactor, etc.

Feeding means (for raw materials, miscellaneous recycled matter, gaseous oxidant, etc.) connected to the oxidation chamber 12 are represented by a single feeding line 18 for purposes of clarity and brevity. However, it should be understood that, in practice, a number of individual lines may be used, including if appropriate, devices such as for example mixing vessels, heaters, coolers, etc.

The oxidation chamber 12 is connected to a dibasic acid precipitation station 22, which is preferably a flash crystallizer, connected to a flash line 24 through which the pressure is relieved to a lower pressure, which is preferably atmospheric, and more preferably sub-atmospheric, thus reducing the temperature in the crystallizer and causing crystallization of crystallizable matter. The dibasic acid precipitation station 22 may be a single-stage or multi-stage flash crystallizer, where the pressure and temperature are reduced consecutively in the different stages. For example, if it is a two stage flash crystallizer (not shown), the pressure may be reduced to atmospheric in the first stage and to sub-atmospheric in the second stage. Additional cooling may be achieved in many ways, including utilization of coolers (not shown), and other methods or devices. Such flash crystallizers are described in detail, for example, in our copending U.S. application Ser. No. 08/824,992, filed Mar. 27, 1997.

The dibasic acid precipitation station 22 is also connected to a dibasic acid separator 26 (through a transfer line 25), which is suited to separate liquids from solids. Examples of separators are centrifugal separators and filtering devices, such as filter-presses for example, among others, very well known to the art. The dibasic acid separator 26 is connected to first solids removal line 27. The separator 26 is also connected to a tank 28 through a first mother liquor line 29. The tank 28 is in turn connected to a de-watering station 30 through transfer line 31. The de-watering station leads to a first thermal treatment station 32 through transfer line 34. The first thermal treatment station 32 is preferably provided with a heater 35. The de-watering station 30 may be in the form of a distillation column 30, which column 30 is provided with an exit line 33, while the first thermal treatment station 32 may be in the form of a heated tank. It should be pointed out that the de-watering station and the first thermal treatment station may be just one unit, or only one of the two stations may be required depending on the circumstances. If the water level of the contents of tank 28, for example, is low enough, heating the reaction mixture to a higher temperature in the first thermal treatment station 32 (even in the absence of the de-watering station 30) may be adequate to cause precipitation of catalyst to a required degree. Similarly, if the temperature at the lower part of a distillation column is adequately high and the water level adequately low, precipitation of catalyst may occur. Further, addition of an anhydride, such as acetic acid anhydride for example, added to the de-watering station 30, or directly to the first catalyst precipitation station 32, can lower the water level so that catalyst precipitates at the prevailing temperature inside the station 32. Our U.S. patent application Ser. No. 08/931,035, filed Sep. 16, 1997, gives a plurality of examples of such devices which may be used as the first catalyst precipitation assembly.

The first thermal treatment station 32 is connected to a first catalyst separator through transfer line 38. The first catalyst separator 36 is provided with a second solids removal line 40 which is preferably connected to the oxidation chamber 12. The first catalyst separator 36 is also connected to a second thermal treatment station 42 through a second mother liquor line 44. The second thermal treatment station 42, being provided with a heater 43, acts also as an evaporator for removing monobasic acid, such as acetic acid for example, through monobasic acid removal line 46. The second thermal treatment station 42 may comprise more than one precipitation chambers, preferably arranged in series, if so desired. Although the monobasic acid removal line 46, may be connected to the oxidation chamber 12 for recycling the monobasic acid either as vapor or as liquid to said oxidation chamber 12, or to any other chamber, it is highly preferable that it is connected to the bottom of the de-watering station 30, in the case a column represents the de-watering station 30. In this manner, the heat contained in the monobasic acid when removed from the second thermal treatment station 42 is released in column 30, thus driving said column 30. The station 42 is further provided with inlet line 48 for adding any desirable adjuncts, such as glutaric acid for example.

The second thermal treatment station 42 is connected to a second catalyst separator 50 through transfer line 52. The catalyst separator 50, which is a hot melt separator, is connected to a third solids removal line 54, which is preferably connected to the tank 28. It is also connected to a third mother liquor line 56, which in turn is connected to a recycle mother liquor line 58 leading back to the second thermal treatment station 42.

In operation of this embodiment, raw materials are fed through line 18 to the oxidation chamber 12, which encloses the oxidation zone 14. Oxidation chambers are well known to the art. According to this invention, in the case of adipic acid manufacture by direct oxidation of cyclohexane, the raw materials are preferably cyclohexane as the hydrocarbon; acetaldehyde or cyclohexanone as the initiator; oxygen, or air, or another gas mixture containing oxygen and inert gases such as nitrogen, as the oxidant; a cobalt compound as catalyst; and acetic acid as the monobasic acid solvent. A small amount of water in the oxidation zone is preferably controlled to be higher than that at or under which catalyst precipitates, but lower than that at or over which a second liquid phase is formed. It is also preferable that the raw materials and the conditions are maintained at a steady state. By the term "steady state", it is meant that the reaction has reached an equilibrium, which equilibrium, however, may be adjusted periodically or continuously in order to achieve a desired result. If for example more water is needed in the reaction or oxidation zone to avoid catalyst precipitation, the water feed rate to the reaction or oxidation zone may be increased appropriately, and still the reaction may be considered to be at a "steady state." Similarly, if less water is needed to avoid formation of two phases, the water feed rate to the reaction or oxidation zone may be decreased appropriately, and still the reaction may be considered to be at a "steady state." The feed rates of the rest of the ingredients or raw materials are also managed in a similar way, whether they are newly introduced or they are products of recycling.

Although it is not absolutely necessary, it is nevertheless highly desirable that before any catalyst precipitation the major part of dibasic acids, in this example adipic acid, possibly with small amounts of glutaric and succinic acids, is removed. This is accomplished in the dibasic acid precipitation chamber 22, preferably by flash crystallization, which, as aforementioned, may be achieved in one or more stages, wherein both temperature and pressure are reduced. The pressure is reduced through line 24, which may lead to vacuum pumps, condensers, and other accessories well known to the art. During flash crystallization, a considerable amount of cyclohexane with a smaller amounts of acetic acid and water are removed through line 24. Of course, flash crystallization may be augmented or replaced by conventional cooling techniques. The slurry produced by the precipitation of the adipic acid, with small amounts of glutaric and succinic acids, is transferred to the dibasic acid separator 26, where the solid dibasic acid matter is separated and leaves the system through the first solids removal line 27. The removed adipic acid may then be recrystallized or otherwise treated. The most common methods of solids separation are centrifugation and filtration.

The liquid remaining after removal of the solid matter, otherwise labeled as the first mother liquor, is transferred to the tank 28. It comprises glutaric acid, succinic acid, adipic acid, acetic acid, and smaller amounts of cyclohexane, water, and other adjuncts, such as esters and other by-products. In tank 28, the first mother liquor is mixed with catalyst solids from the second catalyst separator 50 through the third solids removal line 54. Although the catalyst solids from the second catalyst separator 50, may be treated in any desired way, in a manner to re-utilize the catalyst in the oxidation zone 14 of the oxidation chamber 12, it is highly desirable that the precipitated catalyst be recycled to tank 28. The major reason is that the separated catalyst in line 54 contains mainly salts of the catalyst, cobalt for example, with dibasic acids, such as for example adipic, glutaric, and succinic acids, along with free dibasic acids, in the case of adipic acid manufacture. Since it is not desirable to recycle dibasic acids and dibasic acid salts back to the oxidation chamber 16, the third solids removal line 54 preferably directs these solids to the tank 28. The precipitated solids from the second catalyst precipitator may first be washed with liquids (molten or otherwise) containing little or no dibasic acids (for example a portion of the stream carried through line 33 after condensation), in order for example to remove mother liquor, or for other reasons. Tank 28 contains an abundance of acetic acid along with smaller amounts of water and other matter, provided by the first mother liquor line 29. Due to the acetic acid and water content in tank 28, the dibasic acid catalyst salts, which were insoluble in the molten dibasic acids in the second thermal treatment station 42, re-dissolve and re-equilibrate to form predominantly acetic salt of the catalyst metal in the contents of the tank 28.

In sequence, the contents of the tank 28 are being transferred to the de-watering station 30, which preferably is in the form of a de-hydration column. As the contents of tank 28 move down the column, hot acetic acid, preferably coming from line 46, removes gradually water and other minor components, such as for example cyclohexane, cyclohexanol and cyclohexanone through vapor line 33. The vapors removed through line 33, the great majority of which is monobasic acid, may be recycled to the oxidation chamber 12, or treated otherwise. The liquid mixture at the bottom of the column 30 is being transferred to the first thermal treatment station 32, after having been dehydrated to a desired degree. The higher the dehydration or de-watering degree the higher the percentage of precipitated catalyst in the first thermal treatment station 32 at a set temperature. Of course the set temperature has to be higher than a precipitation temperature at which catalyst precipitates, as described in detail in our copending U.S. patent application Ser. No. 08/931,035, filed Sep. 16, 1997.

It should be pointed out again that removal of water from a mixture includes binding the water in a manner that it is not free to act as water for the purposes of this invention. For example, reaction of an acid anhydride, such as acetic acid anhydride for example, with water contained in a mixture, is considered as water removal from the mixture, or de-watering, or dehydration, despite the fact the oxygen and hydrogen atoms, which constituted the reacted water molecule, are still present in the mixture.

Due to the abundance of monobasic acid, such as acetic acid for example, the major part of the precipitated catalyst (second solids as described herein) is in the form of a salt of the monobasic acid (cobaltous acetate, for example), which after separation in the first catalyst separator 36, is preferably recycled to the oxidation zone 14 of the oxidation chamber 12, through the second solids removal line 40. However, the precipitate may first be washed with liquids containing little or no dibasic acids (for example a portion of the stream carried through line 33 after condensation), in order for example to remove mother liquor, or for other reasons. At this stage, it is preferable to precipitate the major portion of the dissolved catalyst. It is preferable to precipitate over 60%, more preferable over 70%, and even more preferable over 80%.

After separation of the precipitated catalyst in the first catalyst separator 36, the remaining second mother liquor, containing dissolved catalyst, dibasic acids, monobasic acid solvent, and small amounts of other adjuncts, is transferred to the second thermal treatment station 42. At the second thermal treatment station 42, which also acts as an evaporator for removing at least the major part of the monobasic acid solvent, such as acetic acid for example, substantially a major part of the rest of catalyst is precipitated, mainly as dibasic acid salts in molten dibasic acids containing also by-product esters and other minor adjuncts. The removed monobasic acid is preferably recycled to the bottom of the dehydration column 30 through line 46, as aforementioned, for driving the column. If for any reason, the monobasic acid solvent is not recycled to the dehydration column 30, a re-boiler, well known to the art, will be necessary to drive the column.

The second thermal treatment station 42 may be operated at reduced pressure for more efficient evaporation of monobasic acid, or for other reasons. However, the pressure in the second thermal treatment station 42 should preferably maintained higher than the pressure in the de-watering station 30, to avoid compression requirements in line 46.

As already discussed, monobasic acid anhydride, such as acetic acid anhydride for example, may be used in addition to or instead of the dehydration column 30, constituting the de-watering station. The catalyst precipitated in the second thermal treatment station 42 is separated from a third mother liquor in the separator 50 and recycled to tank 28, as mentioned earlier. The molten third mother liquor leaves the system through the third mother liquor line 56. Part of it is recycled to the second thermal treatment station 42 though the recycle mother liquor line 58, and part of it is subjected to further treatment at a later stage (not shown).

It is sometimes desirable to use inlet line 48 for adding into station 42 adjuncts, such as glutaric acid, for example.

Some of the advantages that may be achieved, among others, by following respective teaching of this invention are:

The catalyst is precipitated in two stages, or two catalyst precipitation zones.

In the first catalyst precipitation zone, preferably the majority of catalyst is precipitated by removing water and/or thermally treating the reaction mixture. This is advantageous for two main reasons. One main reason is that the major part of the precipitated catalyst is in the form of a salt with the monobasic acid solvent (cobaltous acetate, for example), so that it may be recycled to the oxidation zone directly without simultaneous recycling of substantial quantities of other products or by-products (dibasic acids or their salts with the catalyst, for example). The second main reason is that by removal of the majority of the catalyst in the first precipitation zone, a workable melt of reasonable viscosity is produced in the second precipitation zone, so that substantially all of the remaining catalyst may be separated easily and effectively, by hot melt filtration or hot melt centrifugation, for example. Without removal of the majority of the catalyst in the first catalyst precipitation zone, an viscous molten mass is received, from which catalyst separation is impractical, if not impossible.

Although the catalyst in the second catalyst precipitation zone is mainly precipitated in the form of salts of catalyst with dibasic acids, recycling of this precipitated catalyst to the first catalyst precipitation zone, wherein there is an abundance of monobasic acid solvent (acetic acid, for example), causes a major part of the catalyst to be re-precipitated as a salt of the catalyst with the monobasic acid solvent (cobaltous acetate, for example), which may be recycled to the oxidation zone, as already mentioned, without substantial recycling of other products and by-products.

The monobasic acid solvent (acetic acid, for example) removed from the second catalyst precipitation zone (by evaporation) may be recycled to the de-watering station of the first catalyst precipitation zone, which may contain a dehydration column, in a manner that it drives the column by providing at least part of the energy it consumed in order to be evaporated. After it removes water in the dehydration column, it may be recycled to the oxidation zone, if so desired.

After separation of the catalyst in the second catalyst separator, part of the molten third mother liquor may be recycled to the second thermal treatment station for reducing further the hot melt viscosity, if so desired. Other adjuncts, such as glutaric acid for example, may also be added to the second thermal treatment station for similar reasons, if so desired.

Any small amount of catalyst after the second catalyst precipitation may be removed, if so desired, by other conventional techniques, such as for example treatment with ion exchange resins, precipitation after addition of compounds forming insoluble salts of the catalyst metal, etc.

It should be understood that according to the present invention, any liquids or gases or off-gases may be recycled totally or partially from any section to any other section, if so desired. Further, any combinations of the exemplifying matter, in part or in total, or any equivalent arrangements or any combinations of equivalent arrangements may be utilized, and are within the scope of the present invention.

Although miscellaneous functions are preferably controlled by a computerized controller, it is possible, according to this invention, to utilize any other type of controller or even manual controls and/or labor for controlling one or more functions. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be taken at each instance. The expert systems are programmed based on the expertise of experienced human beings. The fuzzy logic systems are based on intuition rules in addition to expertise rules.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane. Other examples include preparation of aromatic carboxylic acids such as benzoic acid, phthalic acid, isophthalic acid, and terephthalic acid, among others.

Regarding adipic acid, the preparation of which is especially suited to the methods and apparatuses of this invention, general information may be found in a plethora of U.S. Patents, among other references. These include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Dibasic acids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Examples demonstrating the operation of the instant invention have been given for illustration purposes only, and should not be construed as limiting the scope of this invention in any way. In addition it should be stressed that the preferred examples discussed in detail hereinabove, as well as any other examples encompassed within the limits of the instant invention, may be practiced individually, or in any combination thereof, according to common sense and/or expert opinion. Individual sections of the examples may also be practiced individually or in combination with other individual sections of examples or examples in their totality, according to the present invention. These combinations also lie within the realm of the present invention. Furthermore, any attempted explanations in the discussion are only speculative and are not intended to narrow the limits of this invention.

What is claimed is:

1. A method of removing catalyst from a reaction mixture containing one or more dibasic acids, the reaction mixture having been formed after reaction of a hydrocarbon with an oxidant in the presence of the catalyst, water, and a monobasic acid solvent, in an oxidation zone, the method being characterized by steps of:

(a) precipitating part of the catalyst in a first catalyst precipitation zone by removing water at least partially from the reaction mixture and/or controlling temperature to be adequately high for causing partial catalyst precipitation;

(b) removing the precipitated catalyst, thus forming a second mother liquor comprising dissolved catalyst, monobasic acid solvent, and one or more of dibasic acids;

(c) removing at least partially the monobasic acid solvent and melting the one or more dibasic acids until catalyst precipitates in a second catalyst precipitation zone; and (d) removing the catalyst which precipitated in step (c).

2. A method as defined in claim 1, further comprising a step of recycling the catalyst precipitated in step (b) to the oxidation zone.

3. A method as defined in claim 1, further comprising a step of recycling the catalyst removed in step (d) to the first catalyst precipitation zone.

4. A method as defined in claim 2, further comprising a step of recycling the catalyst removed in step (d) to the first catalyst precipitation zone.

5. A method as defined in claim 1, further comprising a step of partially removing the one or more dibasic acids before step (a).

6. A method as defined in claim 2, further comprising a step of partially removing the one or more dibasic acids before step (a).

7. A method as defined in claim 3, further comprising a step of partially removing the one or more dibasic acids before step (a).

8. A method as defined in claim 4, further comprising a step of partially removing the one or more dibasic acids before step (a).

9. A method as defined in claim 1 wherein the hydrocarbon comprises a compound selected from a group consisting of cyclohexane, cyclohexanone, cyclohexanol, cyclohexylhydroperoxide, and a mixture thereof, the oxidant comprises oxygen, and one of the dibasic acids comprises adipic acid.

10. A method as defined in claim 2 wherein the hydrocarbon comprises a compound selected from a group consisting of cyclohexane, cyclohexanone, cyclohexanol, cyclohexylhydroperoxide, and a mixture thereof, the oxidant comprises oxygen, and one of the dibasic acids comprises adipic acid.

11. A method as defined in claim 3 wherein the hydrocarbon comprises a compound selected from a group consisting of cyclohexane, cyclohexanone, cyclohexanol, cyclohexylhydroperoxide, and a mixture thereof, the oxidant comprises oxygen, and one of the dibasic acids comprises adipic acid.

12. A method as defined in claim 4 wherein the hydrocarbon comprises a compound selected from a group consisting of cyclohexane, cyclohexanone, cyclohexanol, cyclohexylhydroperoxide, and a mixture thereof, the oxidant comprises oxygen, and one of the dibasic acids comprises adipic acid.

13. A method as defined in claim 5 wherein the hydrocarbon comprises a compound selected from a group consisting of cyclohexane, cyclohexanone, cyclohexanol, cyclohexylhydroperoxide, and a mixture thereof, the oxidant comprises oxygen, and one of the dibasic acids comprises adipic acid.

14. A method as defined in claim 6 wherein the hydrocarbon comprises a compound selected from a group consisting of cyclohexane, cyclohexanone, cyclohexanol, cyclohexylhydroperoxide, and a mixture thereof, the oxidant comprises oxygen, and one of the dibasic acids comprises adipic acid.

15. A method as defmed in claim 7 wherein the hydrocarbon comprises a compound selected from a group consisting of cyclohexane, cyclohexanone, cyclohexanol, cyclohexylhydroperoxide, and a mixture thereof, the oxidant comprises oxygen, and one of the dibasic acids comprises adipic acid.

16. A method as defined in claim 8 wherein the hydrocarbon comprises a compound selected from a group consisting of cyclohexane, cyclohexanone, cyclohexanol, cyclohexylhydroperoxide, and a mixture thereof, the oxidant comprises oxygen, and one of the dibasic acids comprises adipic acid.

17. A method as defined in claim 1 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

18. A method as defined in claim 17, further comprising a step of spinning the polymer into fibers.

19. A method as defined in claim 4 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

20. A method as defined in claim 19, further comprising a step of spinning the polymer into fibers.

21. A method as defined in claim 5 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

22. A method as defined in claim 21, further comprising a step of spinning the polymer into fibers.

23. A method as defined in claim 8 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

24. A method as defined in claim 23, further comprising a step of spinning the polymer into fibers.

25. A method as defined in claim 9 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

26. A method as defined in claim 25, further comprising a step of spinning the polymer into fibers.

27. A method as defined in claim 12 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

28. A method as defined in claim 27, further comprising a step of spinning the polymer into fibers.

29. A method as defined in claim 13 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

30. A method as defined in claim 29, further comprising a step of spinning the polymer into fibers.

31. A method as defined in claim 16 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

32. A method as defined in claim 31, further comprising a step of spinning the polymer into fibers.

33. A method as defined in claim 1, further comprising a step of forming a third mother liquor after removing the precipitated catalyst in step (d), and recycling part of the third mother liquor back to the second catalyst precipitation zone.

34. A method as defined in claim 2, further comprising a step of forming a third mother liquor after removing the precipitated catalyst in step (d), and recycling part of the third mother liquor back to the second catalyst precipitation zone.

35. A method as defined in claim 3, further comprising a step of forming a third mother liquor after removing the precipitated catalyst in step (d), and recycling part of the third mother liquor back to the second catalyst precipitation zone.

36. A method as defined in claim 4, further comprising a step of forming a third mother liquor after removing the precipitated catalyst in step (d), and recycling part of the third mother liquor back to the second catalyst precipitation zone.

37. A method as defined in claim 8, further comprising a step of forming a third mother liquor after removing the precipitated catalyst in step (d), and recycling part of the third mother liquor back to the second catalyst precipitation zone.

38. A method as defined in claim 9, further comprising a step of forming a third mother liquor after removing the precipitated catalyst in step (d), and recycling part of the third mother liquor back to the second catalyst precipitation zone.

39. A method as defined in claim 12, further comprising a step of forming a third mother liquor after removing the precipitated catalyst in step (d), and recycling part of the third mother liquor back to the second catalyst precipitation zone.

40. A method as defined in claim 16, further comprising a step of forming a third mother liquor after removing the precipitated catalyst in step (d), and recycling part of the third mother liquor back to the second catalyst precipitation zone.

41. A method as defined in claim 33 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

42. A method as defined in claim 41, further comprising a step of spinning the polymer into fibers.

43. A method as defined in claim 38 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

44. A method as defined in claim 43, further comprising a step of spinning the polymer into fibers.

45. A method as defined in claim 9, further comprising a step of adding glutaric acid to the second catalyst precipitation zone.

46. A method as defined in claim 12, further comprising a step of adding glutaric acid to the second catalyst precipitation zone.

47. A method as defined in claim 16, further comprising a step of adding glutaric acid to the second catalyst precipitation zone.

48. A method as defined in claim 45 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

49. A method as defined in claim 48, further comprising a step of spinning the polymer into fibers.

50. A method as defined in claim 46 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

51. A method as defined in claim 50, further comprising a step of spinning the polymer into fibers.

52. A method as defined in claim 47 wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

53. A method as defined in claim 52, further comprising a step of spinning the polymer into fibers.

54. A method as defined in claim 1, wherein the monobasic acid removed in step (c) is utilized in step (a) for removing the water from the reaction mixture.

55. A method as defined in claim 4, wherein the monobasic acid removed in step (c) is utilized in step (a) for removing the water from the reaction mixture.

56. A method as defined in claim 5, wherein the monobasic acid removed in step (c) is utilized in step (a) for removing the water from the reaction mixture.

57. A method as defined in claim 9, wherein the monobasic acid removed in step (c) is utilized in step (a) for removing the water from the reaction mixture.

58. A method as defined in claim 12, wherein the monobasic acid removed in step (c) is utilized in step (a) for removing the water from the reaction mixture.

59. A method as defined in claim 13, wherein the monobasic acid removed in step (c) is utilized in step (a) for removing the water from the reaction mixture.

60. A method as defined in claim 19, wherein the monobasic acid removed in step (c) is utilized in step (a) for removing the water from the reaction mixture.

61. A method as defined in claim 20, wherein the monobasic acid removed in step (c) is utilized in step (a) for removing the water from the reaction mixture.

* * * * *